(12) United States Patent
Wang et al.

(10) Patent No.: US 11,428,677 B2
(45) Date of Patent: Aug. 30, 2022

(54) REFERENCE FINGERPRINT OF VIRGIN OLIVE OIL, AND ESTABLISHMENT METHOD AND APPLICATION THEREOF

(71) Applicant: Longnan Xiangyu Olive Development Co., Ltd., Gansu (CN)

(72) Inventors: Bo Wang, Longnan (CN); Yuhong Liu, Longnan (CN); Jianke Li, Longnan (CN); Feng Jin, Longnan (CN); Xiaoping Zhou, Longnan (CN); Yongqing Yang, Longnan (CN); Gongpeng Wu, Longnan (CN); Min Zhao, Longnan (CN); Huijun Wang, Longnan (CN); Huan Zhang, Longnan (CN)

(73) Assignee: LONGNAN XIANGYU OLIVE DEVELOPMENT CO., LTD., Longnan (CN)

( * ) Notice: Subject to any disclaimer, the term of this patent is extended or adjusted under 35 U.S.C. 154(b) by 231 days.

(21) Appl. No.: 16/819,943

(22) Filed: Mar. 16, 2020

(65) Prior Publication Data
US 2021/0123894 A1    Apr. 29, 2021

(30) Foreign Application Priority Data
Oct. 25, 2019    (CN) .......................... 201911021945.0

(51) Int. Cl.
*G01N 30/74*    (2006.01)
*G01N 1/38*    (2006.01)
(Continued)

(52) U.S. Cl.
CPC .............. *G01N 30/74* (2013.01); *G01N 1/38* (2013.01); *G01N 33/03* (2013.01); *G01N 2030/027* (2013.01)

(58) Field of Classification Search
CPC .......... G01N 30/74; G01N 1/38; G01N 33/03; G01N 2030/027; G01N 30/8686; G01N 2030/8813; G01N 30/02
See application file for complete search history.

(56) References Cited

U.S. PATENT DOCUMENTS

2009/0111104 A1 *    4/2009    Karuso ................ G01N 33/582
                                                                                435/6.15

FOREIGN PATENT DOCUMENTS

| CN | 104237409 A | * | 12/2014 | |
| CN | 108459038 B | * | 3/2020 | ............. G01N 24/08 |
| EP | 1952148 A1 | * | 8/2008 | ............... C12Q 1/34 |

\* cited by examiner

*Primary Examiner* — Francis C Gray
(74) *Attorney, Agent, or Firm* — Alston & Bird LLP

(57) ABSTRACT

The present invention provides a reference fingerprint of virgin olive oil, and an establishment method and an application thereof. By using UPLC-FLD, the chromatographic information of various components in the extra virgin olive oil is obtained, breaking through the limitation of establishment of fingerprints by means of conventional GC-MS method and based on the fatty acid composition of edible oil, and further solving the problem that traditional fingerprints only use a single component for determination and thus result in false positivity. Meanwhile, similarity calculation is conducted on the chromatographic information of serial extra virgin olive oil, establishing a reference fingerprint of virgin olive oil, reinforcing the polymorphism of fingerprint information, reflecting its differences from edible oil from the perspectives of the substance composition, distribution, and content of virgin olive oil, helping improve accuracy of identification, and enabling rapid, convenient and accurate identification of the quality of virgin olive oil.

16 Claims, 3 Drawing Sheets

(51) Int. Cl.
*G01N 33/03* (2006.01)
*G01N 30/02* (2006.01)

REFERENCE FINGERPRINT OF VIRGIN OLIVE OIL, AND ESTABLISHMENT METHOD AND APPLICATION THEREOF

CROSS-REFERENCE TO RELATED APPLICATIONS

This application claims priority to Chinese Patent Application No. 201911021945.0, filed on Oct. 25, 2019, the entire contents of which are incorporated herein by reference.

TECHNICAL FIELD

The present invention relates to the field of detection technique, and in particular to a reference fingerprint of virgin olive oil, and an establishment method and an application thereof.

BACKGROUND

Olive oil is a type of oil obtained from fresh olives (not including oils obtained by solvent extraction or re-esterification process) and undoped with other types of oils and fats. Virgin olive oil is of the highest quality and nutritive value, which is rich in such natural active substances as unsaturated fatty acids, squalene, polyphenol, and vitamins, and plays roles in antioxidation, cholesterol regulation, cancer prevention, and cosmetology, with far higher price compared with other edible vegetable oils. With unique physicochemical properties and superb nutritional and healthcare effects, olive oil is favored by people. In view of this, some merchants are prompted by economic interests, resulting in always serious problems with adulterate olive oil. So far, there are two most pervasive types of problems with adulteration of olive oil: one is that cheap vegetable oil is mixed with expensive olive oil; the other is that low-grade virgin olive oil or pomace olive oil is added into extra virgin olive oil.

Because of difficulty in adulteration identification of olive oil, related testing and trade standards are not far enough to satisfy practical requirements. Conventional adulteration identification and detection method of virgin olive oil is to determine the quality or identity of the olive oil by means of detection of quality and characteristic indexes (acid value, peroxide value, residual solvent, fatty acid composition, unsaponifiable matters, and ultraviolet absorbance). In addition, one of the most commonly used standard method for identifying adulteration of olive oil internationally is sterol analysis. However, this method has problems with complex sample pretreatment process, many interference factors, poor reproducibility, and long detection cycle. Olive oil identification methods reported include near-infrared spectroscopy, determination of the wax content, nuclear magnetic resonance (NMR) spectroscopy, and GC-MS method. All of these methods play active roles to some extent, but the complexity of adulteration of olive oil and different indexes of other adulterated vegetable oils challenge the foregoing analytical method and often bring a lot of confusion to identification. Therefore, it is necessary to develop a relatively stable, practical, and highly accurate adulteration identification method with reference to the fingerprint of virgin olive oil, in order to fight against such undesirable phenomena as shoddy and adulterate olive oil.

A standard fingerprint is a spectrum representing common characteristics of fingerprints of a batch of samples of the same type. Research on fatty acid fingerprints is the most widely and deeply studied so far. However, some studies have shown that some vegetable oils have a similar fatty acid composition. Therefore, there is some risk associated with identification and characterization of these oils and fats with similar fatty acid composition by means of fatty acid fingerprints; also, using fatty acid fingerprints to identify adulterate oils merely has the possibility of misjudgment because the type and extent of adulteration are also large.

SUMMARY

In view of this, the objective of the present invention is to provide a reference fingerprint of virgin olive oil, and an establishment method and an application thereof. The reference fingerprint of virgin olive oil provided by the present invention can evaluate the quality of virgin olive oil rapidly and accurately.

To achieve the above purpose, the present invention provides the following technical solution.

The present invention provides an establishment method of a reference fingerprint of virgin olive oil, including the following steps:

mixing 10-30 batches of extra virgin olive oil with a solvent for extraction, to obtain serial extra virgin olive oil samples;

conducting ultra-performance liquid chromatography-fluorescence detection (UPLC-FLD) on the extra virgin olive oil samples, to obtain the chromatographic information of the serial extra virgin olive oil samples;

conducting similarity calculation on the chromatographic information of the serial extra virgin olive oil samples, and obtaining the reference fingerprint of the virgin olive oil.

Preferably, the solvent is methanol, acetonitrile, or ethanol.

Preferably, the consumption ratio of the extra virgin olive oil to the solvent is 1.0-5.0 g:5-20 mL.

Preferably, conditions of the UPLC-FLD include:
column: RP-$C_{18}$ column or SVEA $C_{18}$ column;
flow rate: 0.1-0.4 mL/min;
excitation wavelength: 300 nm;
emission wavelength: 350 nm;
column temperature: 25-40° C.;
injection volume: 0.1-3.0 µL;
mobile phase: A is 0.0-0.3% (v/v) formic acid-methanol or 0.0-0.3% (v/v) formic acid-acetonitrile; B is 0.05-0.3% (v/v) formic acid-water;
the gradient elution program is:
0-3 min: 10% A, 90% B; and
3-45 min: 55% A, 45% B.

Preferably, the software for similarity calculation is Similarity Evaluation System for Chromatographic Fingerprint of TCM (Version A) published by the Chinese Pharmacopoeia Commission.

Preferably, the area of a fingerprint peak in the reference fingerprint of virgin olive oil is greater than 5%.

The present invention further provides a reference fingerprint of virgin olive oil obtained by the above establishment method.

The present invention further provides an application of the above reference fingerprint of virgin olive oil in the field of detection of quality of virgin olive oil.

Preferably, the application includes the following steps:
mixing the virgin olive oil with a solvent for extraction, to obtain a virgin olive oil solution;

conducting ultra-performance liquid chromatography-fluorescence detection (UPLC-FLD) on the virgin olive oil solution, to obtain the chromatographic information of the virgin olive oil solution;

with reference to the reference fingerprint of virgin olive oil, conducting similarity calculation on the chromatographic information of the virgin olive oil solution, to achieve the purpose of evaluating the quality of virgin olive oil.

Preferably, the application further includes:

dissolving coumarin, hydroxytyrosol, vanillic acid, and salicylic acid standards in a solvent, to obtain a mixed standard solution of coumarin, hydroxytyrosol, vanillic acid, and salicylic acid;

conducting UPLC-FLD on the mixed standard solution, to obtain the chromatographic information of the mixed standard solution;

with reference to the chromatographic information of the mixed standard solution, assigning the chromatographic information of the virgin olive oil solution.

The present invention provides an establishment method of reference fingerprint of virgin olive oil, including the following steps: mixing 10-30 batches of extra virgin olive oil with a solvent for extraction, to obtain serial extra virgin olive oil samples; conducting ultra-performance liquid chromatography-fluorescence detection (UPLC-FLD) on the extra virgin olive oil samples, to obtain the chromatographic information of the serial extra virgin olive oil samples; conducting similarity calculation on the chromatographic information of the serial extra virgin olive oil samples, and obtaining the reference fingerprint of the virgin olive oil. In the present invention, serial extra virgin olive oil samples are analyzed using UPLC-FLD, and the chromatographic information of various components in the extra virgin olive oil is obtained, breaking through the limitation of establishment of fingerprints by means of conventional GC-MS method and based on the fatty acid composition of edible oil, and further solving the problem that traditional fingerprints only use a single component for determination and thus result in false positivity. Meanwhile, similarity calculation is conducted on the serial extra virgin olive oil, establishing a reference fingerprint of virgin olive oil based on common peaks, reinforcing the polymorphism of reference fingerprint information, reflecting its differences from edible oil from the perspectives of the substance composition, distribution, and content of virgin olive oil, helping improve accuracy of identification, and enabling rapid, convenient and accurate identification of the quality of virgin olive oil. It possesses high application value in routine quality analysis of virgin olive oil and inspections for market supervision and industrial production.

The present invention further provides an application of the reference fingerprint of virgin olive oil provided in the foregoing technical solution in the field of detection of quality of virgin olive oil. The reference fingerprint of virgin olive oil established by the present invention can evaluate the quality of virgin olive oil more sensitively and accurately due to a number of reference peaks.

DETAILED DESCRIPTION

Figure 1:
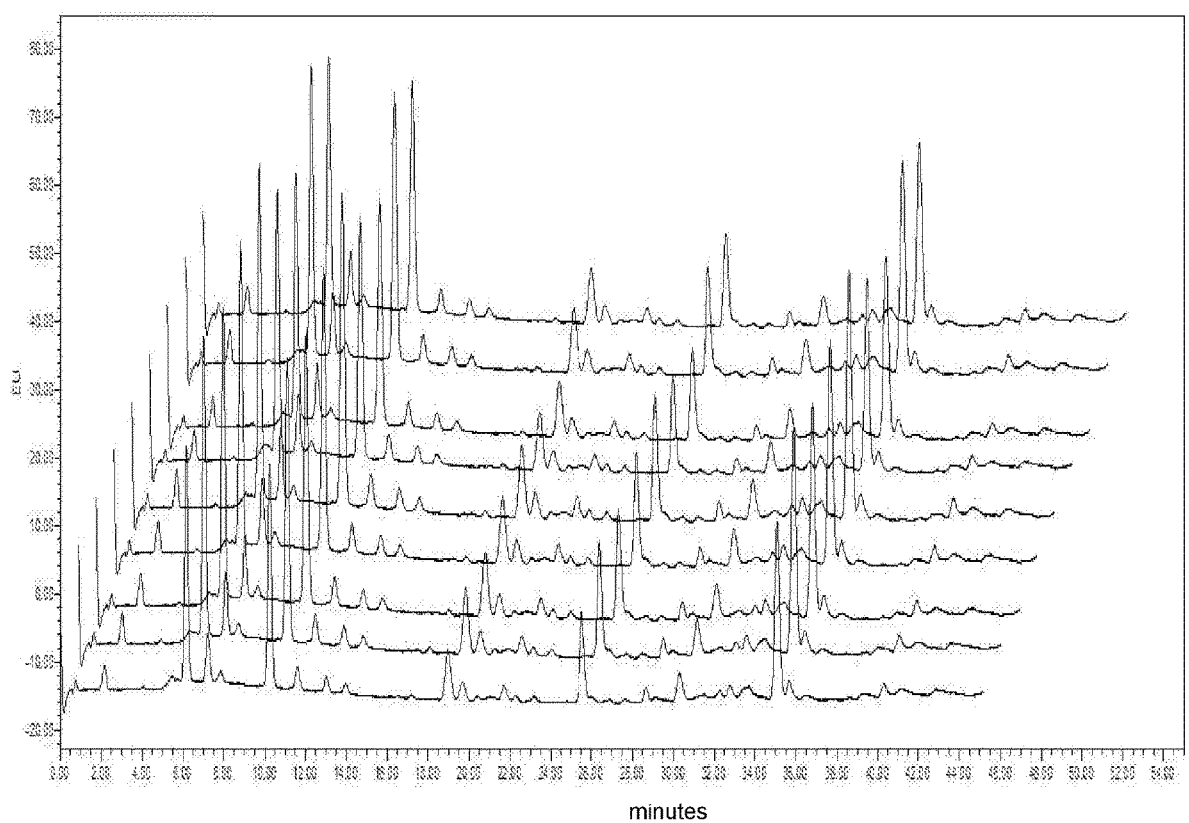
FIG. 1 shows an overlapping chromatogram of the chromatographic information of nine extra virgin olive oil samples.

The present invention provides an establishment method of reference fingerprint of virgin olive oil, including the following steps:

mixing 10-30 batches of extra virgin olive oil with a solvent for extraction, to obtain serial extra virgin olive oil samples;

conducting ultra-performance liquid chromatography-fluorescence detection (UPLC-FLD) on the extra virgin olive oil samples, to obtain the chromatographic information of the serial extra virgin olive oil samples;

conducting similarity calculation on the chromatographic information of the serial extra virgin olive oil samples, to obtain the reference fingerprint of the virgin olive oil.

In the present invention, 10-30 batches of extra virgin olive oil are mixed with a solvent for extraction, in order to obtain serial extra virgin olive oil samples.

In the present invention, the extra virgin olive oil is the one without any other substances, and reference fingerprint peaks obtained by such extra virgin olive oil have maximum accuracy. The source of the extra virgin olive oil is not specifically limited in the present invention, but the virgin olive oil without any other substances that those skilled in the art can obtained may be used.

In the present invention, the consumption ratio of the extra virgin olive oil to the solvent is preferably 1.0-5.0 g:5-20 mL; the solvent is preferably methanol, acetonitrile, or ethanol.

In the present invention, the mixing is preferably conducted in a polyethylene tube. In the present invention, the extracting means is preferably vortex extraction; the vortex extraction time is preferably 2-120 s, and more preferably 120 s.

After extraction, the present invention further preferably includes: centrifuging the resulting extract, and then filtering supernatant to obtain the extra virgin olive oil samples. In the present invention, the centrifugal rotational speed is preferably 5000-15000 r/min, and more preferably 10000 r/min; the centrifugal time is preferably 10-30 min, and more preferably 20 min; the filter membrane is preferably 0.22 μm organic microporous membrane.

After serial extra virgin olive oil samples are obtained, UPLC-FLD is conducted on the extra virgin olive oil samples in the present invention, in order to obtain the chromatographic information of the serial extra virgin olive oil samples.

In the present invention, conditions of the UPLC-FLD include:

column is preferably RP-$C_{18}$ column or SVEA C18 column, and more preferably SVEA $C_{18}$ column;

flow rate is preferably 0.1-0.4 mL/min, and more preferably 0.3 mL/min;

excitation wavelength is preferably 300 nm;

emission wavelength is preferably 350 nm;

column temperature is preferably 25-40° C., and more preferably 30° C.;

injection volume is preferably 0.1-3.0 μL, and more preferably 0.1 μL;

mobile phase: A is preferably 0.0-0.3% (v/v) formic acid-methanol or 0.0-0.3% (v/v) formic acid-methanol or formic acid-acetonitrile, and more preferably 0.1% (v/v)

formic acid-methanol; B is preferably 0.05-0.3% (v/v) formic acid-water, and more preferably 0.1% (v/v) formic acid-water;

the gradient elution program is preferably:
0-3 min: 10% A, 90% B; and
3-45 min: 55% A, 45% B.

After the chromatographic information of the serial extra virgin olive oil samples is obtained, similarity calculation is conducted on the chromatographic information of the serial extra virgin olive oil samples in the present invention, and the reference fingerprint of the virgin olive oil is obtained.

In the present invention, the software for similarity calculation is Similarity Evaluation System for Chromatographic Fingerprint of TCM (Version A) published by the Chinese Pharmacopoeia Commission.

In the present invention, area of fingerprint peak in the reference fingerprint of virgin olive oil is preferably greater than 5%. In the present invention, the fact that the area of a fingerprint peak in the reference fingerprint of virgin olive oil is preferably greater than 5% ensures more chromatographic information in the reference fingerprint, and the peak area being greater than 5% avoids the effect of impurity peaks, improving the accuracy of the reference fingerprint.

The present invention further provides a reference fingerprint of virgin olive oil obtained by the establishment method provided in the foregoing technical solution. In the present invention, the area of fingerprint peak in the reference fingerprint of virgin olive oil is preferably greater than 5%.

The reference fingerprint of virgin olive oil provided in the present invention is an analysis of extra virgin olive oil based on UPLC-FLD, by which chromatographic information of many substances in the extra virgin olive oil is obtained, followed by similarity computation of the chromatographic information of serial extra virgin olive oil samples to acquire a common mode as the reference fingerprint of virgin olive oil; meanwhile, in the reference fingerprint of extra virgin olive oil, all chromatographic information with peak area greater than 5% will reflect on the reference fingerprint of virgin olive oil, improving the accuracy of the reference fingerprint.

The present invention further provides an application of the reference fingerprint of virgin olive oil provided in the foregoing technical solution in the field of detection of quality of virgin olive oil.

In the present invention, the application includes the following steps:

mixing the virgin olive oil with a solvent for extraction, to obtain a virgin olive oil solution;

conducting UPLC-FLD on the virgin olive oil solution, to obtain the chromatographic information of the virgin olive oil solution;

with reference to the reference fingerprint of virgin olive oil, conducting similarity calculation on the chromatographic information of the virgin olive oil solution, to achieve the purpose of evaluating the quality of virgin olive oil.

In the present invention, the virgin olive oil is mixed with a solvent for extraction, in order to obtain a virgin olive oil solution.

In the present invention, the type, consumption, mixing and extracting means of the solvent is preferably consistent with those parameters at the time of preparing serial extra virgin olive oil samples when establishing the reference fingerprint of virgin olive oil. Thus, the details will not be repeated herein.

After the virgin olive oil solution is obtained, the UPLC-FLD is conducted on the virgin olive oil solution in the present invention, and the chromatographic information of the virgin olive oil solution is obtained.

In the present invention, the parameters of the UPLC-FLD are consistent with those parameters at the time of UPLC-FLD when establishing the reference fingerprint of virgin olive oil. Thus, the details will not be repeated herein.

After the chromatographic information of the virgin olive oil solution is obtained, with reference to the reference fingerprint of virgin olive oil in the present invention, similarity calculation is conducted on the chromatographic information of the virgin olive oil solution, in order to achieve the purpose of evaluating the quality of virgin olive oil.

In the present invention, the software for similarity calculation is preferably consistent with the similarity software used when establishing the reference fingerprint of virgin olive oil. Thus, the details will not be repeated herein.

In the present invention, the application further preferably includes:

dissolving coumarin, hydroxytyrosol, vanillic acid, and salicylic acid standards in a solvent, to obtain a mixed standard solution of coumarin, hydroxytyrosol, vanillic acid, and salicylic acid;

conducting UPLC-FLD on the mixed standard solution, to obtain the chromatographic information of the mixed standard solution;

with reference to the chromatographic information of the mixed standard solution, assigning the chromatographic information of the virgin olive oil solution.

In the present invention, all concentrations of coumarin, hydroxytyrosol, vanillic acid, and salicylic acid in the mixed standard solution of coumarin, hydroxytyrosol, vanillic acid, and salicylic acid are preferably 50-5000 mg/L, and more preferably 100 mg/L.

In the present invention, the parameters of the UPLC-FLD are consistent with those parameters at the time of UPLC-FLD when establishing the reference fingerprint of virgin olive oil. Thus, the details will not be repeated herein.

Use of the reference fingerprint of virgin olive oil provided by the present invention can determine the quality of virgin olive oil roundly, objectively and accurately, which not only effectively evaluates the overall quality of virgin olive oil to ensure the legitimate rights and interests of consumers, but also detects its active components quantitatively, providing theoretical and data supports.

The reference fingerprint of virgin olive oil and the establishment method and application thereof provided by the present invention will be described below in detail in conjunction with the embodiment, but they should not be construed as limiting the protection scope of the invention.

Parameters of UPLC-FLD conducting in the following embodiment are:

column is SVEA C18 column; for mobile phase, A is 0.1% formic acid-methanol, and B is 0.1% formic acid-water; flow rate is 0.3 mL/min; excitation wavelength is 300 nm; emission wavelength is 350 nm; column temperature is 30° C.; injection volume is 0.1 pt. Gradient elution conditions are shown in Table 1. After running, equilibrate for 3-10 min under initial conditions.

TABLE 1

Gradient elution conditions

| Time (t/min) | Mobile Phase A (%) | Mobile Phase B (%) |
|---|---|---|
| 0-3 | 10 | 90 |
| 3-45 | 55 | 45 | volumetric flask to prepare a mixed standard solution of coumarin, hydroxytyrosol, vanillic acid, and salicylic acid (all of which were 100 mg/L); UPLC-FLD was conducted on the mixed standard solution, and a chromatogram of the mixed standard solution was obtained.

Figure 2:
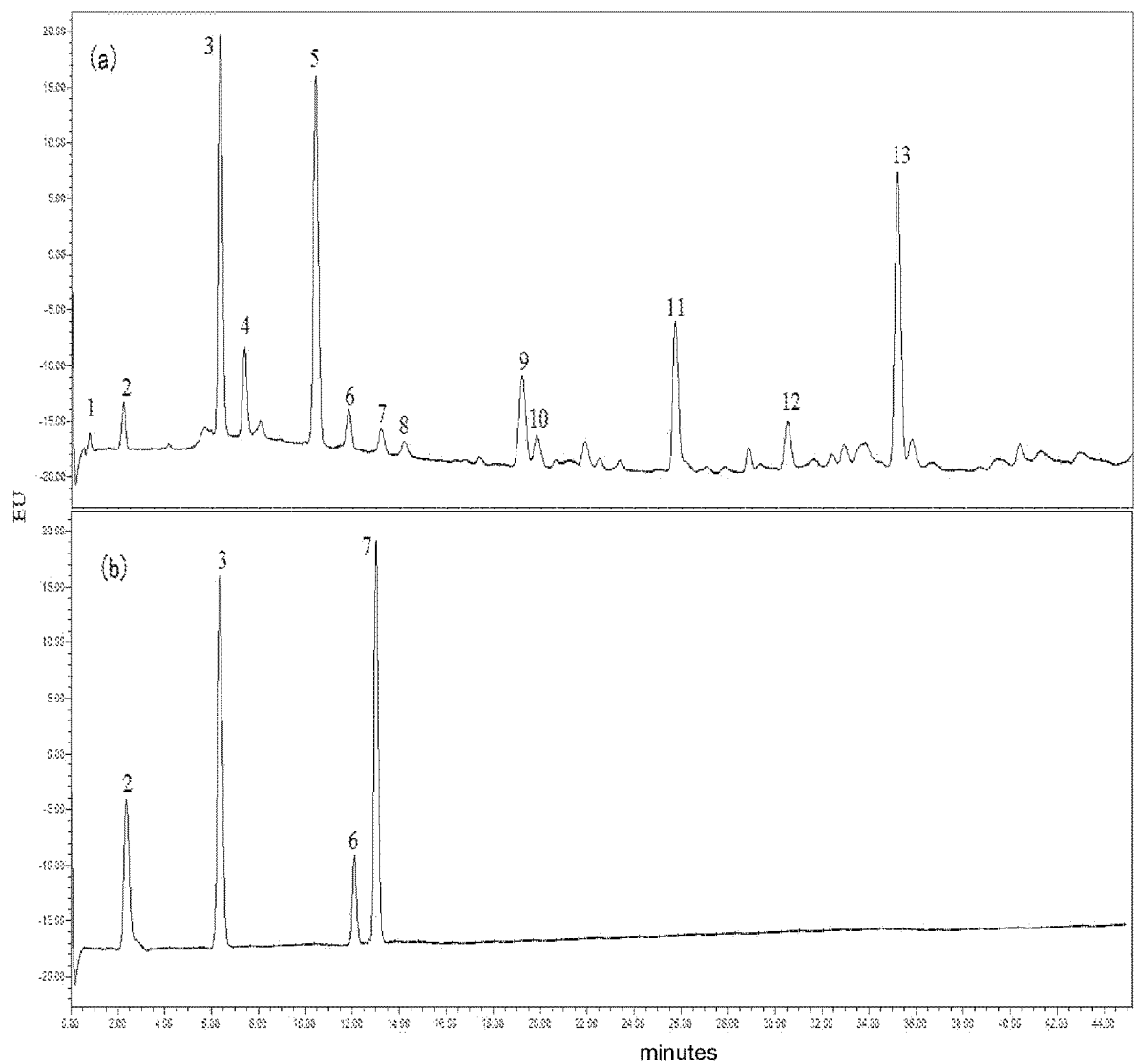
FIG. 2 shows a reference fingerprint of virgin olive oil (a) and a chromatogram of a mixed standard solution (b)

FIG. 2 shows a reference fingerprint of the virgin olive oil (a) and a chromatogram of the mixed standard solution (b). As seen from FIG. 2: peak 2 in the reference fingerprint of the virgin olive oil is hydroxytyrosol; peak 3 is vanillic acid; peak 6 is salicylic acid; and peak 7 is coumarin.

Table 2 shows the similarity data of the chromatographic information of 17 extra virgin olive oil samples.

TABLE 2

The similarity data of the chromatographic information of 17 extra virgin olive oil samples

|  | S1 | S2 | S3 | S4 | S5 | S6 | S7 | S8 | S9 | S10 | S11 | S12 | S13 | S14 | S15 | S16 | S17 | R |
|---|---|---|---|---|---|---|---|---|---|---|---|---|---|---|---|---|---|---|
| S1 | 1 | 0.999 | 0.993 | 1 | 1 | 0.993 | 0.999 | 1 | 0.985 | 0.982 | 0.999 | 0.999 | 0.994 | 0.999 | 0.998 | 0.984 | 0.997 | 0.999 |
| S2 | 0.999 | 1 | 0.993 | 1 | 0.999 | 0.993 | 0.999 | 1 | 0.985 | 0.983 | 0.999 | 0.999 | 0.994 | 0.999 | 0.998 | 0.984 | 0.997 | 0.999 |
| S3 | 0.993 | 0.993 | 1 | 0.993 | 0.993 | 1 | 0.989 | 0.993 | 0.976 | 0.973 | 0.989 | 0.989 | 1 | 0.989 | 0.988 | 0.972 | 0.987 | 0.989 |
| S4 | 1 | 1 | 0.993 | 1 | 1 | 0.993 | 0.999 | 1 | 0.985 | 0.982 | 0.999 | 0.999 | 0.994 | 0.999 | 0.998 | 0.983 | 0.997 | 0.999 |
| S5 | 1 | 0.999 | 0.993 | 1 | 1 | 0.993 | 0.999 | 1 | 0.985 | 0.982 | 0.999 | 0.999 | 0.994 | 0.999 | 0.998 | 0.984 | 0.997 | 0.999 |
| S6 | 0.993 | 0.993 | 1 | 0.993 | 0.993 | 1 | 0.989 | 0.993 | 0.976 | 0.973 | 0.989 | 0.989 | 1 | 0.989 | 0.988 | 0.972 | 0.987 | 0.989 |
| S7 | 0.999 | 0.999 | 0.989 | 0.999 | 0.999 | 0.989 | 1 | 0.999 | 0.987 | 0.985 | 0.999 | 0.999 | 0.99 | 0.999 | 0.999 | 0.984 | 0.998 | 1 |
| S8 | 1 | 1 | 0.993 | 1 | 1 | 0.993 | 0.999 | 1 | 0.985 | 0.982 | 0.999 | 0.999 | 0.994 | 0.999 | 0.998 | 0.983 | 0.997 | 0.999 |
| S9 | 0.985 | 0.985 | 0.976 | 0.985 | 0.985 | 0.976 | 0.987 | 0.985 | 1 | 0.997 | 0.986 | 0.986 | 0.977 | 0.986 | 0.987 | 0.968 | 0.985 | 0.987 |
| S10 | 0.982 | 0.983 | 0.973 | 0.982 | 0.982 | 0.973 | 0.985 | 0.982 | 0.997 | 1 | 0.983 | 0.983 | 0.974 | 0.982 | 0.986 | 0.968 | 0.986 | 0.984 |
| S11 | 0.999 | 0.999 | 0.989 | 0.999 | 0.999 | 0.989 | 0.999 | 0.999 | 0.986 | 0.983 | 1 | 1 | 0.99 | 1 | 0.999 | 0.983 | 0.998 | 1 |
| S12 | 0.999 | 0.999 | 0.989 | 0.999 | 0.999 | 0.989 | 0.999 | 0.999 | 0.986 | 0.983 | 1 | 1 | 0.99 | 1 | 0.999 | 0.984 | 0.998 | 1 |
| S13 | 0.994 | 0.994 | 1 | 0.994 | 0.994 | 1 | 0.99 | 0.994 | 0.977 | 0.974 | 0.99 | 0.99 | 1 | 0.99 | 0.989 | 0.974 | 0.988 | 0.991 |
| S14 | 0.999 | 0.999 | 0.989 | 0.999 | 0.999 | 0.989 | 0.999 | 0.999 | 0.986 | 0.982 | 1 | 1 | 0.99 | 1 | 0.998 | 0.983 | 0.997 | 1 |
| S15 | 0.998 | 0.998 | 0.988 | 0.998 | 0.998 | 0.988 | 0.999 | 0.998 | 0.987 | 0.986 | 0.999 | 0.999 | 0.989 | 0.998 | 1 | 0.986 | 0.999 | 0.999 |
| S16 | 0.984 | 0.984 | 0.972 | 0.983 | 0.984 | 0.972 | 0.984 | 0.983 | 0.968 | 0.968 | 0.983 | 0.984 | 0.974 | 0.983 | 0.986 | 1 | 0.984 | 0.984 |
| S17 | 0.997 | 0.997 | 0.987 | 0.997 | 0.997 | 0.987 | 0.998 | 0.997 | 0.985 | 0.986 | 0.998 | 0.998 | 0.988 | 0.997 | 0.999 | 0.984 | 1 | 0.998 |
| R | 0.999 | 0.999 | 0.989 | 0.999 | 0.999 | 0.989 | 1 | 0.999 | 0.987 | 0.984 | 1 | 1 | 0.991 | 1 | 0.999 | 0.984 | 0.998 | 1 |

R: presents the reference fingerprint generated by fingerprint software

Embodiment 1

1.1. Establishment of Reference Fingerprint of Virgin Olive Oil 1.1.1. Ten grams (10.0 g) of 17 batches of extra virgin olive oil was weighed accurately and placed in a 50 mL polyethylene (PE) tube; 20 mL of methanol was added precisely; after vortex extraction for 1.0 min and centrifugation at 10000 r/min, 1.5 mL of supernatant was pipetted and filtered through a 0.22 μm organic microporous membrane to obtain 17 extra virgin olive oil samples.

1.1.2. UPLC-FLD was conducted on the 17 extra virgin olive oil samples, and chromatographic information of the 17 extra virgin olive oil samples was acquired. FIG. 1 shows an overlapping chromatogram with chromatographic information of 9 of the 17 extra virgin olive oil samples.

1.1.3. Similarity was calculated on chromatographic information of the 17 extra virgin olive oil samples, and a reference fingerprint of the virgin olive oil was obtained. In the chromatographic information of the 17 extra virgin olive oil samples, chromatographic peaks with >5% of peak area were set up as fingerprint peaks. Finally, 13 common fingerprint peaks were selected to establish the reference fingerprint of the virgin olive oil.

Ten milligrams (mg) each of coumarin, hydroxytyrosol, vanillic acid, and salicylic acid standards were accurately weighed, dissolved in methanol, and diluted in a 100 mL 1.2. Application of the Reference Fingerprint of Virgin Olive Oil UPLC-FLD was conducted on the virgin olive oil mixed with different concentrations of soybean oil (5%-50%, v/v), and the chromatographic information of the virgin olive oil mixed with different concentrations of soybean oil (5%-50%, v/v) was obtained.

With reference to the reference fingerprint of the virgin olive oil obtained from step 1.1.3. and using a similarity software, similarity computation was conducted on the chromatographic information of the virgin olive oil mixed with different concentrations of soybean oil (5%-50%, v/v). Results are shown in Table 3.

TABLE 3

The similarity data for the virgin olive oil mixed with different concentrations of soybean oil (5%-50%, v/v)

| Soybean oil concentration | Similarity |
|---|---|
| 5.0% | 0.881 |
| 10.0% | 0.805 |
| 15.0% | 0.745 |
| 20.0% | 0.612 |
| 25.0% | 0.568 |
| 30.0% | 0.503 |
| 35.0% | 0.411 |
| 40.0% | 0.343 |
| 45.0% | 0.304 |
| 50.0% | 0.231 |

As seen from Table 3: there is a great difference in similarity between the chromatographic information of the virgin olive oil mixed with different concentrations of soybean oil (5%-50%, v/v) and the reference fingerprint of virgin olive oil obtained from step 1.1.3., indicating that this method can provide reference data for identifying the virgin olive oil mixed with different concentrations of soybean oil (5%-50%, v/v).

Figure 3:
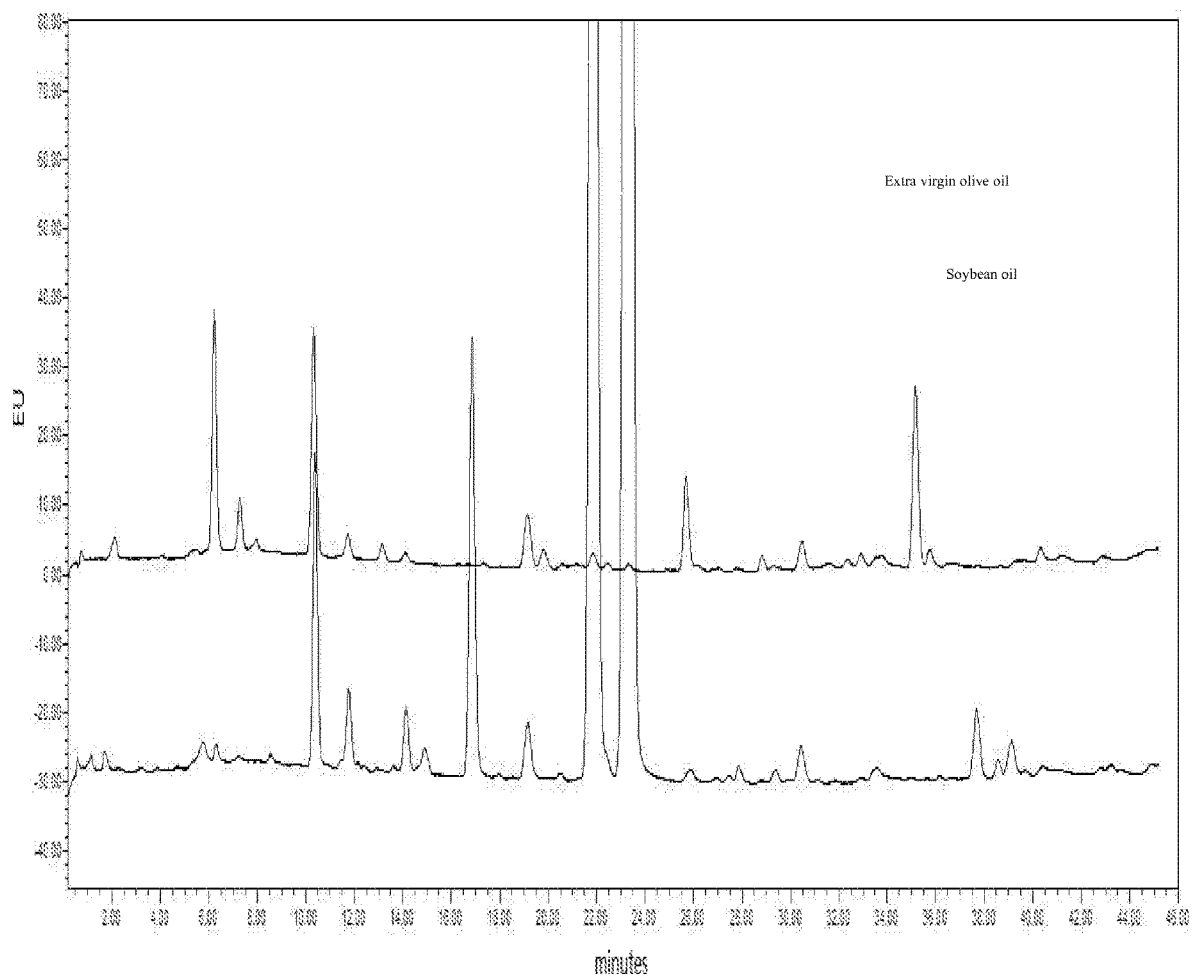
FIG. 3 shows a chromatogram of extra virgin olive oil versus soybean oil.

UPLC-FLD was conducted on both extra virgin olive oil and soybean oil, and a chromatogram of extra virgin olive oil versus soybean oil was obtained. Results are shown in FIG. 3. As seen from FIG. 3: there is a great difference in chromatographic information between extra virgin olive oil and soybean oil.

1.3. Precision Test

Ten grams (10.0 g) of extra virgin olive oil was measured. The sample was treated according to step "1.1.1.", followed by UPLC-FLD. Six consecutive runs were injected. The retention time of major chromatographic peaks and the relative standard deviation (RSD) were 0.90%-2.91% and 2.44%-3.91%, respectively. The data showed that the instrument precision could satisfy the experimental requirement.

1.4. Reproducibility Test

Ten grams (10.0 g) of extra virgin olive oil was measured. The sample was treated according to step "1.1.1.", followed by UPLC-FLD. The retention time of major chromatographic peaks and the relative standard deviation (RSD) were 0.83%-2.02% and 1.83%-3.13%, respectively. The data showed that this method had good reproducibility and could satisfy the experimental requirement.

1.5. Stability Test

Ten grams (10.0 g) of extra virgin olive oil was measured. The sample was treated according to step "1.1.1.", and extra virgin olive oil samples were obtained; at room temperature, UPLC-FLD was conducted on extra virgin olive oil samples at 0, 4, 8, 16, 24, and 48 h after treatment. The retention time of major chromatographic peaks and the relative standard deviation (RSD) were 2.14%-3.06% and 1.91%-3.85%, respectively, indicating that extra virgin olive oil samples were stable within 48 h.

The foregoing descriptions are only preferred implementation manners of the present invention. It should be noted that for a person of ordinary skill in the art, several improvements and modifications may further be made without departing from the principle of the present invention. These improvements and modifications should also be deemed as falling within the protection scope of the present invention.

What is claimed is:

1. A method for establishing a reference fingerprint of extra virgin olive oil, comprising the following steps:
    mixing 10-30 batches of extra virgin olive oil with a solvent and extracting extra virgin olive oil samples, wherein the extracting is conducted by vortex extraction for 2 to 120 seconds;
    conducting ultra-performance liquid chromatography-fluorescence detection (UPLC-FLD) on the extra virgin olive oil samples, to obtain the chromatographic information of the extra virgin olive oil samples;
    conducting similarity calculation on the chromatographic information of the extra virgin olive oil samples to obtain the reference fingerprint of the extra virgin olive oil.

2. The establishment method according to claim 1, wherein the solvent is methanol, acetonitrile, or ethanol.

3. The method according to claim 1, wherein the consumption a ratio of the extra virgin olive oil to the solvent is 1.0-5.0 g:5-20 mL.

4. The method according to claim 1, wherein the UPLC-FLD is performed under the following conditions:
    column: RP-$C_{18}$ column or SVEA $C_{18}$ column;
    flow rate: 0.1-0.4 mL/min;
    excitation wavelength: 300 nm;
    emission wavelength: 350 nm;
    column temperature: 25-40° C.;
    injection volume: 0.1-3.0 μL;
    mobile phase: A is 0.0-0.3% (v/v) formic acid-methanol or 0.0-0.3% (v/v) formic acid-acetonitrile; B is 0.05-0.3% (v/v) formic acid-water; and
    gradient elution program: eluting for 0-3 min with 10% A and 90% B, and the for another 3-45 min with 55% A and 45% B.

5. A reference fingerprint of extra virgin olive oil obtained by the method according to claim 1.

6. An application of the reference fingerprint of extra virgin olive oil according to claim 5 in the field of detection of quality of virgin olive oil.

7. The application according to claim 6, comprising the following steps:
    mixing the virgin olive oil with a solvent for extraction, to obtain a virgin olive oil solution;
    conducting ultra-performance liquid chromatography-fluorescence detection (UPLC-FLD) on the virgin olive oil solution, to obtain the chromatographic information of the virgin olive oil solution;
    with reference to the reference fingerprint of extra virgin olive oil, conducting similarity calculation on the chromatographic information of the virgin olive oil solution, to evaluate the quality of virgin olive oil.

8. The application according to claim 7, further comprising:
    dissolving coumarin, hydroxytyrosol, vanillic acid, and salicylic acid standards in a solvent, to obtain a mixed standard solution of coumarin, hydroxytyrosol, vanillic acid, and salicylic acid;
    conducting UPLC-FLD on the mixed standard solution, to obtain the chromatographic information of the mixed standard solution;
    with reference to the chromatographic information of the mixed standard solution, assigning the chromatographic information of the virgin olive oil solution.

9. The method according to claim 2, wherein a ratio of the extra virgin olive oil to the solvent is 1.0-5.0 g:5-20 mL.

10. A reference fingerprint of extra virgin olive oil obtained by the method according to claim 2.

11. A reference fingerprint of extra virgin olive oil obtained by the method according to claim 3.

12. A reference fingerprint of extra virgin olive oil obtained by the method according to claim 4.

13. A reference fingerprint of extra virgin olive oil obtained by the method according to claim 5.

14. An application of the reference fingerprint of extra virgin olive oil according to claim 7 in the field of detection of quality of virgin olive oil.

15. An 8 of the reference fingerprint of extra virgin olive oil according to claim 10 in the field of detection of quality of virgin olive oil.

16. An application of the reference fingerprint of extra virgin olive oil according to claim 9 in the field of detection of quality of virgin olive oil.

* * * * *